(12) United States Patent
Mori et al.

(10) Patent No.: US 8,802,426 B2
(45) Date of Patent: Aug. 12, 2014

(54) METHOD AND DEVICE FOR ASSAY

(75) Inventors: Mikinaga Mori, Kanagawa-ken (JP);
Junichi Katada, Kanagawa-ken (JP);
Takayoshi Oyamada, Kanagawa-ken (JP); Hideyuki Karaki, Kanagawa-ken (JP); Masayasu Konishi, Kanagawa-ken (JP); Hiroki Terada, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 31 days.

(21) Appl. No.: 13/262,526

(22) PCT Filed: Mar. 30, 2010

(86) PCT No.: PCT/JP2010/056121
§ 371 (c)(1),
(2), (4) Date: Nov. 16, 2011

(87) PCT Pub. No.: WO2010/114145
PCT Pub. Date: Oct. 7, 2010

(65) Prior Publication Data
US 2012/0058465 A1 Mar. 8, 2012

(30) Foreign Application Priority Data

Mar. 30, 2009 (JP) .................. 2009-081388

(51) Int. Cl.
*B01L 3/00* (2006.01)
*G01N 33/543* (2006.01)

(52) U.S. Cl.
CPC ................. *G01N 33/54386* (2013.01)
USPC .................. 435/287.6; 435/283.1; 435/287.1; 436/514; 436/518; 422/420; 422/50

(58) Field of Classification Search
USPC .......................... 436/164–172, 518
See application file for complete search history.

(56) References Cited

U.S. PATENT DOCUMENTS

| 4,918,025 A | 4/1990 | Grenner |
| 5,137,808 A * | 8/1992 | Ullman et al. ................. 435/7.9 |

(Continued)

FOREIGN PATENT DOCUMENTS

| CN | 1781022 A | 5/2006 |
| CN | 1938577 A | 3/2007 |

(Continued)

OTHER PUBLICATIONS

Japanese Office Action dated Jun. 4, 2013 issued in Japanese Patent Application No. 2009-081388.

(Continued)

*Primary Examiner* — Melanie Y Brown
*Assistant Examiner* — Rebecca Martinez
(74) *Attorney, Agent, or Firm* — Sughrue Mion, PLLC

(57) ABSTRACT

A device for assay can evenly develop solution, and performs highly accurate and sensitive measurement. A first device part (10) maintains a second insoluble carrier (12) and a third insoluble carrier (13) in such a manner that they overlap with each other at a detection portion (14) of a first insoluble carrier (11). These three carriers (11), (12) and (13) are housed not in contact with each other. A pressing unit (18) having a pressing surface (18*a*) that is parallel to the detection portion (14) is provided on an inner surface of the second device part (20) facing the detection portion (14). The pressing surface (18*a*) is displaced by being pressed toward the detection portion (14), and presses, from the upper side of the first insoluble carrier (11), the second insoluble carrier (12) and the third insoluble carrier (13) onto the first insoluble carrier (11). The first device part (10) and the second device part (20) are joined together.

1 Claim, 4 Drawing Sheets

(56) References Cited

U.S. PATENT DOCUMENTS

| | | | |
|---|---|---|---|
| 5,726,010 A * | 3/1998 | Clark | 435/5 |
| 5,726,013 A | 3/1998 | Clark | |
| 6,017,494 A | 1/2000 | Ashihara et al. | |
| 7,300,802 B2 * | 11/2007 | Paek et al. | 436/514 |
| 2004/0214253 A1 | 10/2004 | Paek et al. | |
| 2006/0292035 A1 * | 12/2006 | Gould et al. | 422/58 |
| 2007/0273884 A1 * | 11/2007 | Matsushita et al. | 356/445 |
| 2009/0066339 A1 * | 3/2009 | Glezer et al. | 324/444 |

FOREIGN PATENT DOCUMENTS

| | | |
|---|---|---|
| CN | 101098956 A | 1/2008 |
| EP | 0281201 A1 | 3/1988 |
| JP | H01502526 A | 8/1989 |
| JP | H10177028 A | 6/1998 |
| JP | 2001021562 A | 1/2001 |
| JP | 3237540 B2 | 12/2001 |
| JP | 3309977 B2 | 7/2002 |
| JP | 2002202307 A | 7/2002 |
| JP | 2003114225 A | 4/2003 |
| JP | 2006524815 A | 11/2006 |
| JP | 2008286590 A | 11/2008 |
| JP | 2009014690 A | 1/2009 |
| JP | 2010071827 A | 4/2010 |
| JP | 2010071828 A | 4/2010 |
| WO | WO 03/025573 * | 3/2003 |

OTHER PUBLICATIONS

A chromatographic strip test for rapid detection of one lineage of the H5 subtype of high pathogenic avian influenza; Cui Shangjin, et al.; Journal of Veterinary Diagnostic Investigation: Official Publication of the American Association of Veterinary Laboratory Diagnosticians, Inc., Sep. 2008; vol. 20, No. 5; Sep. 2008.

European Search Report; Application No. 10758910.3-1408/2414834 PCT/JP2010056121; Apr. 24, 2013.

Japanese Office Action issued Aug. 20, 2013 in corresponding Japanese Patent Application No. 2009-081388.

Chinese Office Action issued Aug. 15, 2013 in corresponding Chinese Patent Application No. 2010800152790.

* cited by examiner

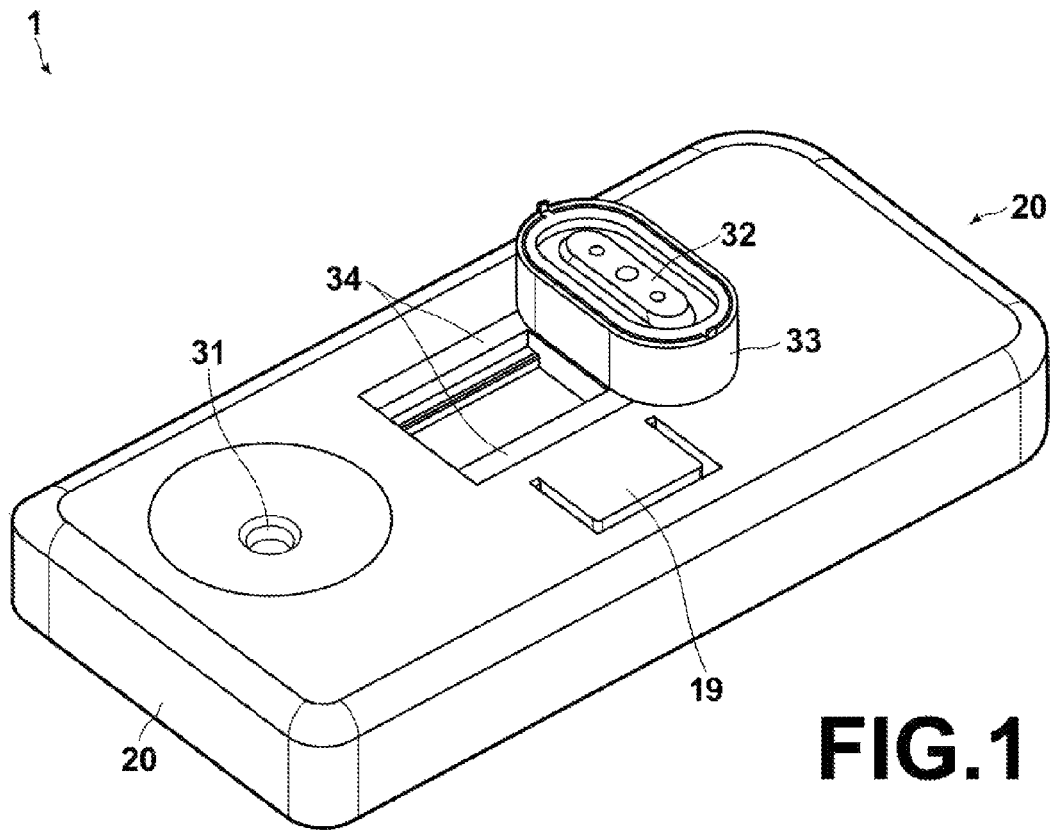
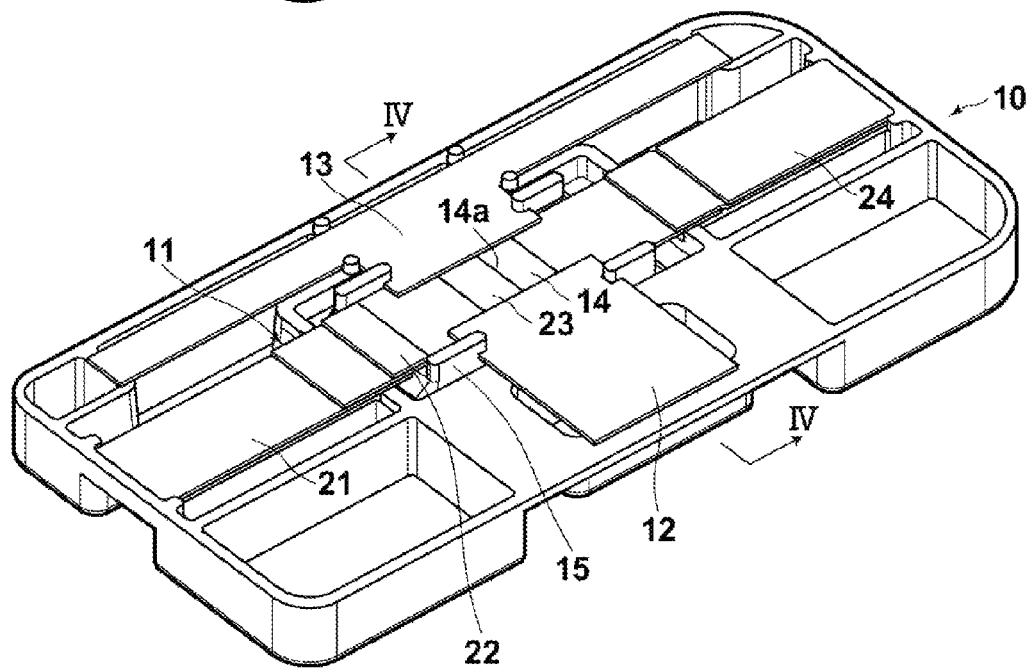
FIG.1

METHOD AND DEVICE FOR ASSAY

CROSS REFERENCE TO RELATED APPLICATIONS

This application is a National Stage of International Application No. PCT/JP2010/056121, filed on Mar. 30, 2010, which claims priority from Japanese Patent Application No. 2009-081388, filed Mar. 30, 2009, the contents of all of which are incorporated herein by reference in their entirety.

TECHNICAL FIELD

The present invention relates to a method for assay and a device for assay that can perform highly sensitive and highly accurate qualitative analyses and quantitative analyses on samples containing analytes.

BACKGROUND ART

In recent years, various kinds of devices that are simple and that can detect analytes (a substance to be detected) contained in sample solutions by developing the sample solutions therein were proposed. Further, in-vitro diagnostic reagents and various kinds of devices for poison detection or the like were sold. One of the examples is a device using immunochromatography. In immunochromatography, no heavy equipment/instrument is required to perform judgment and measurement, and the operation is simple. In immunochromatography, a measurement result can be obtained merely by dropping a sample solution that may contain an analyte onto a carrier, and by keeping the sample solution standing for approximately 5 to 10 minutes. Therefore, the immunochromatography is a simple and quick method, and judgment and measurement with high specificity is possible. Hence, the immunochromatography is widely used, for example, in clinical laboratory examinations at hospitals, laboratory tests for research, and the like.

Meanwhile, many of bioactive substances, such as natural products, toxins, hormones, and pesticides, and environmental pollutants act on living organisms, even if the amounts of the substances are extremely small and even undetectable by using a conventional general immunochromatography method. Therefore, an immunochromatography method that can detect such substances quickly, easily and at high sensitivity is needed. For that purpose, in addition to simply dropping a sample solution containing an analyte onto a carrier, the following method is used to detect the analyte, for example. After the sample solution containing the analyte is dropped onto the carrier to immobilize the analyte on the carrier, the sample solution is washed away by a washing solution (washing liquid). Further, the immobilized analyte is placed in contact with a reaction substrate solution, an amplification solution or the like to detect amplified signals output from the analyte.

For example, Japanese Unexamined Patent Publication No. 2002-202307 (Patent Document 1) discloses an immunochromatography that can analyze an analyte at high sensitivity. In the method, an amplification solution, such as metal colloid, is dropped onto a detection portion. Further, Japanese Patent No. 3309977 (Patent Document 2) discloses a method for detecting signals. In the method, after a sample solution containing an analyte is placed in contact with an enzyme labeled antibody, the sample solution is caused to flow to a stationary phase carrier to which an analyte capture reagent has bound. Accordingly, the analyte—enzyme labeled antibody binds onto the carrier. Further, an enzyme substrate solution is caused to flow to the stationary phase carrier to make the enzyme substrate react, and signals are detected.

In the immunochromatography disclosed in Patent Document 1 and Patent Document 2, signals can be amplified by enzymes or silver. Therefore, it is possible to analyze a very small amount of analyte.

However, in the immunochromatography disclosed in Patent Document 1 and Patent Document 2, components of enzyme substrate solutions, signal amplification solutions, such as metal colloid amplification solutions, or other solutions, such as washing solution, may not be sent to the stationary phase carrier evenly, because of a difference in molecular mutual action, such as hydrophilicity/hydrophobicity and electrostatic mutual actions, with the stationary phase carrier. Therefore, it is difficult to make the reaction progress evenly or uniformly in the stationary phase carrier. Hence, highly accurate and highly sensitive detection is limited.

DISCLOSURE OF THE INVENTION

In view of the foregoing circumstances, it is an object of the present invention to provide an assay method and a device for assay that can evenly develop solution (liquid) and perform highly accurate and highly sensitive measurement.

An assay method of the present invention is an assay method for performing a qualitative or quantitative analysis on an analyte contained in a sample solution, the method comprising the steps of:

sending the sample solution containing at least one kind of analyte to a detection portion on an insoluble carrier, the detection portion containing a substance that specifically binds to the analyte; and sending at least one of a test reagent solution, an amplification solution, and a detection solution to the detection portion, wherein the at least one of the test reagent solution, the amplification solution, and the detection solution is injected to be loaded into a clearance between the insoluble carrier and a member having a surface that faces the insoluble carrier.

A device for assay of the present invention is a device for assay, the device comprising:

a complex part including a first device part and a second device part, wherein the first device part includes a first insoluble carrier housed therein, the first insoluble carrier having a detection portion containing a substance that specifically binds to the analyte, and wherein the second device part has a hole for injecting solution into the first device part, and wherein the second device part includes a portion having a surface that faces the detection portion of the first insoluble carrier.

A device for assay of the present invention may be a device comprising:

a complex part including a first device part and a second device part, wherein the first device part includes a first insoluble carrier housed therein, the first insoluble carrier having a detection portion containing a substance that specifically binds to an analyte, and wherein the second device part has a hole for injecting solution into the first device part, and wherein a second insoluble carrier for developing the solution and a third insoluble carrier for absorbing the solution are housed in the complex part, and wherein the second insoluble carrier and the third insoluble carrier are kept in such a manner that the second insoluble carrier and the third insoluble, carrier overlap with each other at the detection portion of the first insoluble carrier, and wherein the first insoluble carrier, the second insoluble carrier and the third insoluble carrier are housed in such a manner that they are not in contact with each other, and wherein a pressing unit having a pressing surface that faces the detection portion of the first insoluble carrier is provided in the second device part that faces the detection portion of the first insoluble carrier, and wherein the pressing surface is displaced by being pressed toward the detection portion, and presses, from the upper side of the first insoluble carrier, the second insoluble carrier and the third insoluble carrier onto the first insoluble carrier.

When the pressing portion has been pressed toward the detection portion, it is desirable that a clearance between the detection portion and the pressing surface is in the range of 0.01 to 1 mm.

It is desirable that a rib that regulates the displacement of the pressing surface by abutting a part of the pressing unit is provided on an inner surface of the first device part, the inner surface facing the pressing unit.

It is desirable that a solution storage pot that can send solution to the clearance between the detection portion and the pressing surface is provided in at least one of the first device part and the second device part. Further, it is desirable that the solution storage pot is sealed with a laminated film, and that an amplification solution containing silver ions has been injected into the solution storage pot.

In the assay method of the present invention, a qualitative or quantitative analysis is performed on an analyte contained in a sample solution by sending the sample solution containing at least one kind of analyte, and at least one of a test reagent solution, an amplification solution, and a detection solution to a detection portion on an insoluble carrier, the detection portion containing a substance that specifically binds to the analyte. In the assay method, when the at least one of the test reagent solution, the amplification solution, and the detection solution is injected to be loaded into a clearance between the insoluble carrier and a member having a surface that faces the insoluble carrier, it is possible to evenly develop the solution by capillary action or force of the clearance. Therefore, highly accurate and highly sensitive measurement is possible.

BRIEF DESCRIPTION OF THE DRAWINGS

FIG. 1 is a schematic diagram illustrating a separated state of a device for assay according to an embodiment of the present invention;

BEST MODE FOR CARRYING OUT THE INVENTION

Figure 2:
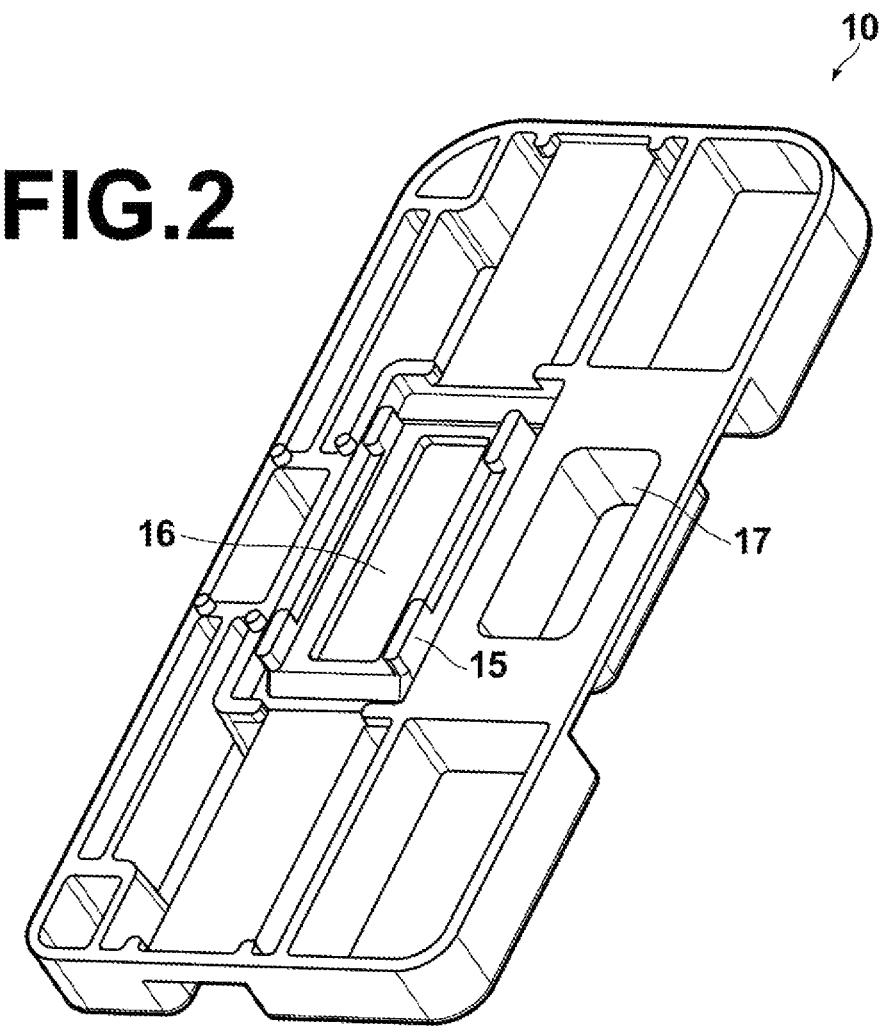
FIG. 2 is a schematic diagram illustrating the structure of a first device part before an insoluble carrier is loaded therein.
Figure 3:
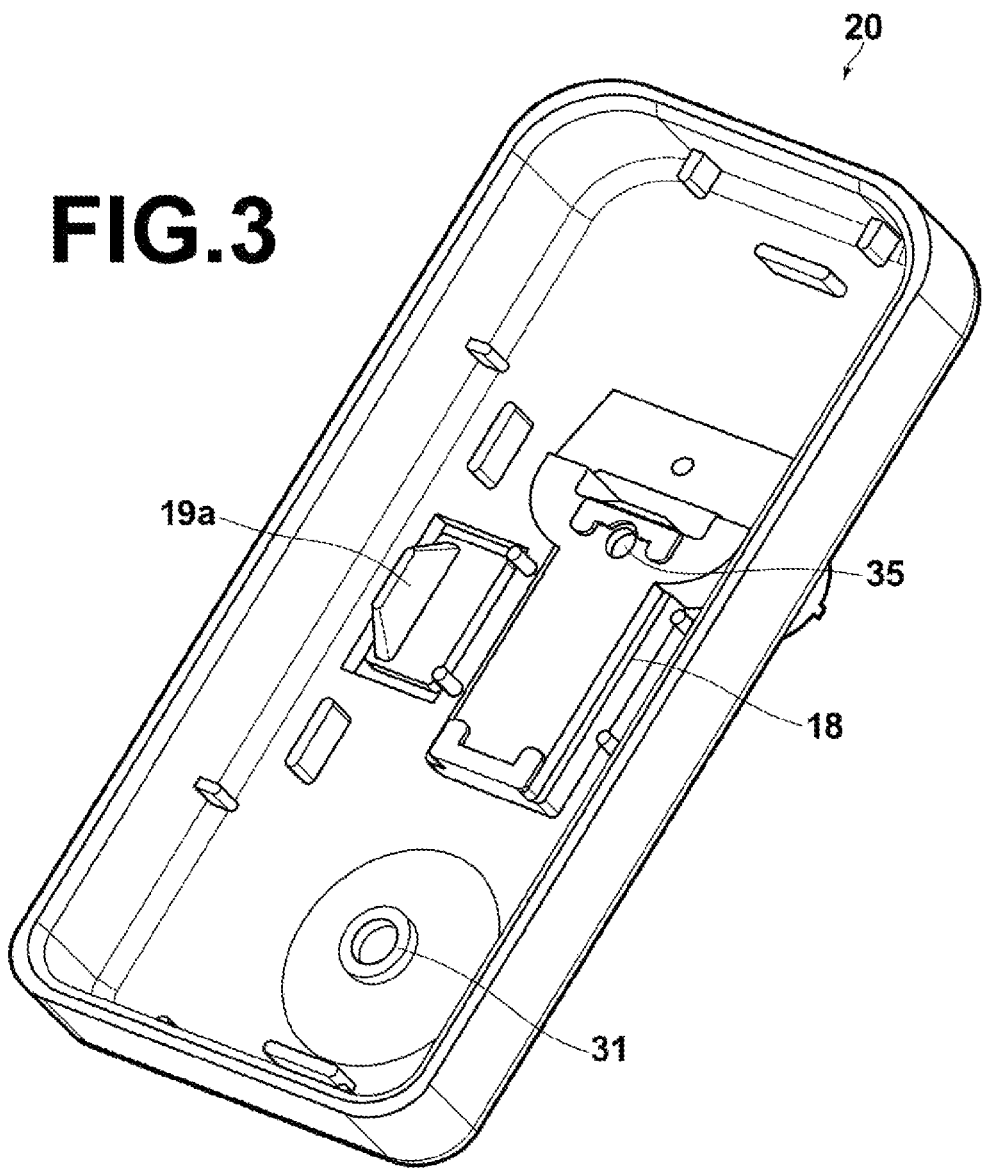
FIG. 3 is a schematic diagram illustrating the structure of the inner surface of a second device part.
Figure 4:
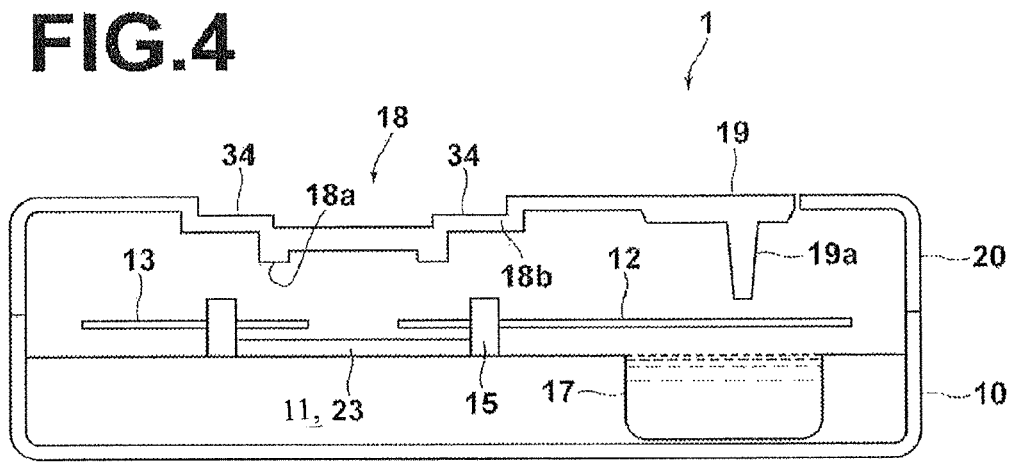
FIG. 4 is a diagram illustrating the cross-section along line IV-IV in FIG. 1.

Hereinafter, a device for assay according to an embodiment of the present invention will be described in detail with reference to drawings. FIG. 1 is a schematic diagram illustrating an example of a device for assay of the present invention. FIG. 1 illustrates a separate state of the device for assay that can perform immunoassay (immunological assay). FIG. 2 is a schematic diagram illustrating the structure of a first device part before an insoluble carrier is loaded therein. FIG. 3 is a schematic diagram illustrating the structure of the inner surface of a second device part. FIG. 4 is a diagram illustrating a cross-section of the device along line IV-IV in FIG. 1. In the following descriptions, a sandwich assay is used as an example of the immunoassay. However, the embodiment of the present invention is not particularly limited to the sandwich assay. The present invention may appropriately be applied to other kinds of immunoassay, such as a competitive assay.

As illustrated in FIG. 1, a device 1 for assay of the present invention includes a first device part 10 and a second device part 20 that are joined together in a vertical direction. The first device part 10 houses a first insoluble carrier 11, a second insoluble carrier 12 for developing solution (spreading or distributing solution or liquid) and a third insoluble carrier for absorbing solution (liquid). The first insoluble carrier 11 has a detection portion 14 containing a specifically binding substance, which specifically binds to an analyte.

The first device part 10 maintains the second insoluble carrier 12 and the third insoluble carrier 13 by recesses (cuts, or notches) of ribs 15 provided on the sides of the first insoluble carrier 11. The second insoluble carrier 12 and the third insoluble carrier 13 are kept in such a manner that they overlap with each other at the detection portion 14 of the first insoluble carrier 11. Further, as illustrated in FIG. 4, the first insoluble carrier 11, the second insoluble carrier 12 and the third insoluble carrier 13 are housed in such a manner that they are not in contact with each other. Further, as illustrated in FIG. 2, an observation window 16 for observing the detection portion 14 of the first insoluble carrier 11 from the outer surface (outside) of the first device part 10 (the back or bottom side of the device 1 for assay) is provided under the first insoluble carrier 11. Further, a washing solution storage pot 17 is provided under the second insoluble carrier 12, and the upper portion of the washing solution storage pot 17 is sealed with a laminated film.

On the outer surface of the second device part 20, a sample solution injection hole 31 and an amplification solution storage pot receiving portion 33 are provided. The sample solution injection hole 31 is used to inject a sample solution containing an analyte toward the first insoluble carrier 11 that is housed in the first device part 10. An amplification solution storage pot 32 for supplying an amplification solution to the first insoluble carrier 11 is set in the amplification solution storage pot receiving portion 33. The amplification solution storage pot 32 is sealed with a laminated film in a state in which the amplification solution storage pot 32 is loaded with an amplification solution. The amplification solution storage pot 32 is set in the amplification solution storage pot receiving portion 33 in such a manner that the sealed portion of the amplification solution storage pot 32 faces downward. Further, a seal-breaking projection portion (not illustrated) is provided in the amplification solution storage pot receiving portion 33. When the amplification solution loaded in the amplification solution storage pot 32 is supplied to the first insoluble carrier, if the amplification solution storage pot 32 is pressed down, the seal-breaking projection portion can break the laminated film of the amplification solution storage pot 32.

Further, as illustrated in FIGS. 3 and 4, a pressing unit 18 having a pressing surface 18a is provided on the inner surface of the second device part 20. The pressing unit 18 faces the detection portion 14 of the first insoluble carrier 11, and the pressing surface 18a is parallel to the detection portion 14 of the first insoluble carrier 11. When the pressing unit 18 is pressed toward the detection portion 14, the pressing surface 18a is displaced, and the second insoluble carrier 12 and the third insoluble carrier 13 are pressed, from the upper side of the first insoluble carrier 11, onto the first insoluble carrier 11 so that they are in contact with the first insoluble carrier 11. Further, the pressing unit 18 forms a clearance (gap) between the first insoluble carrier 11 and the pressing surface 18*a*.

Further, an amplification solution injection hole 35 is provided on the inner surface of the second device part 20. The amplification solution injection hole 35 is provided at a position corresponding to the amplification solution storage pot receiving portion 33. When the seal-breaking projection portion breaks the laminated film of the amplification solution storage pot 32, the amplification solution in the amplification solution storage pot 32 is sent out, through the amplification solution injection hole 35, to the clearance formed between the first insoluble carrier 11 and the pressing surface 18*a*. The amplification solution injection hole 35 is provided at a position so that the amplification solution is sent to the detection portion 14 of the first insoluble carrier 11 in the first device part 10.

Pressing portions 34 are provided on the outer surface of the second device part 20. The pressing portions 34 are provided at corresponding positions of the pressing unit 18. Further, a seal-breaking portion 19*a* for breaking the laminated film that seals the upper portion of the washing solution storage pot 17 is provided on the inner surface of the second device part 20. The seal-breaking portion 19*a* is provided at a position facing the washing solution storage pot 17 in the first device part 10. Further, a seal-breaking unit 19 for pressing down the seal-breaking portion 19*a* is provided on the outer surface of the second device part 20.

The first insoluble carrier 11 includes a sample addition pad 21, a labeling-substance rataining pad 22, a chromatography carrier 23, and an absorption pad 24. A sample solution is dropped onto the sample addition pad 21. A labeling substance that can bind to an analyte or a specifically binding substance, which specifically binds to the analyte, has been immobilized in the labeling-substance rataining pad 22. The chromatography carrier 23 includes the detection portion 14 containing the substance that specifically binds to the analyte. The absorption pad 24 absorbs sample solution sent to the absorption pad 24. Here, to simplify descriptions, a case in which only a single detection line 14*a* is provided in the detection portion 14 will be described. However, a plurality of detection lines, each containing a different specifically binding substance, may be provided. When the plurality of detection lines are provided, a plurality of kinds of analytes contained in the sample solution can be detected in one assay (process). Further, a portion (control portion or region) in which a specifically binding substance for control has been immobilized may be provided in the chromatography carrier 23, if desirable.

Next, the procedure of a method for detecting an analyte by using the device for assay of the present invention will be described. Here, a case in which a sample solution is used as a solution, and a washing solution and an amplification solution are used as test reagent solutions will be described as an example. First, the sample solution is injected through the sample solution injection hole 31 of the second device part 20, and dropped by spot application onto the sample addition pad 21 of the first insoluble carrier 11 housed in the first device part 10. The dropped sample solution is sent toward the labeling-substance rataining pad 22 by capillary force of the first insoluble carrier 11. Since the labeling-substance rataining pad 22 contains a labeling substance that can bind to the analyte, the analyte in the sample solution is labeled with the labeling substance while the sample solution is sent through the labeling-substance rataining pad 22.

The labeled analyte further moves toward the chromatography carrier 23 by capillary force, and captured at the detection line 14*a*, which is a portion in which a specifically-binding substance has been immobilized. Specifically, a complex of (specifically-binding substance)—analyte—(labeling substance) is formed at the detection line 14*a*. The analyte that has not been captured at the detection line 14*a*, unreacted labeling substance that has not bound to the analyte, and the like are absorbed by the absorption pad 24. In the step of sending the sample solution, the first insoluble carrier 11 is in contact neither with the second insoluble carrier 12 nor with the third insoluble carrier 13, as illustrated in FIG. 4. Since the first insoluble carrier 11 is in contact neither with the second insoluble carrier 12 nor with the third insoluble carrier 13, it is possible to send the sample solution only to the first insoluble carrier 11. The sample solution does not infiltrate into the second insoluble carrier 12 and the third insoluble carrier 13. Hence, it is possible to capture the sample solution at the detection line 14*a* without wasting the sample solution, the amount of which is small and limited.

Figure 5:
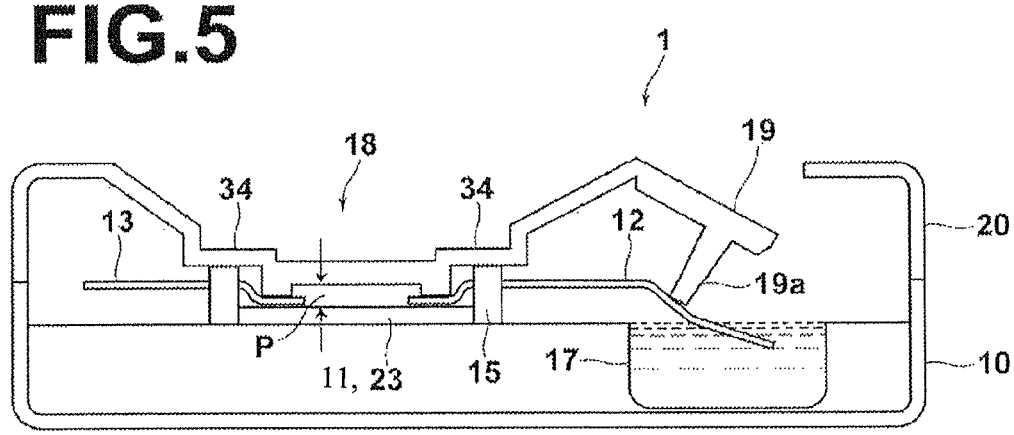
FIG. 5 is a schematic cross-sectional diagram illustrating a state in which both of a pressing unit and a seal-breaking unit have been pressed.

Next, unreacted labeling substance that has not specifically bound to the analyte and remains at the detection line 14*a* and the like are removed from the chromatography carrier 23 by washing. The process will be described with reference to FIG. 5. FIG. 5 is a schematic cross-sectional diagram illustrating a state in which both of the pressing unit and the seal-breaking unit in FIG. 4 are pressed. In the washing step, the pressing portions 34, which are provided on the outer surface of the second device part 20, are pressed toward the first device part 10. Accordingly, the pressing surface 18*a* of the pressing unit 18, which is provided on the inner surface of the second device part 20, is displaced, and the chromatography carrier 23 becomes partially in contact with the second insoluble carrier and the third insoluble carrier 13.

At this time, the displacement of the pressing surface 18*a* is regulated, because recesses 18*b* formed in the pressing unit 18 abut the ribs 15. Therefore, clearance (gap) P is formed between the chromatography carrier 23 and the pressing surface 18*a*. It is desirable that the clearance P is approximately in the range of 0.01 to 1 mm. When the clearance is less than 0.01 mm, it is difficult to make the amplification solution or the like, which will be described later, infiltrate into the clearance. When the clearance is greater than 1 mm, the capillary force does not act, and it is difficult to evenly develop the washing solution, the amplification solution and the like. Therefore, it is desirable that the ribs 15 and the pressing unit 18 are structured in such a manner that the clearance between the chromatography carrier 23 and the pressing surface 18*a* is within the aforementioned range.

Meanwhile, the washing solution storage pot 17 in the first device part 10 is loaded with washing solution. When the seal-breaking unit 19 provided on the outer surface of the second device part 20 is pressed, the seal-breaking portion 19*a* breaks the laminated film that seals the upper portion of the washing solution storage pot 17. Further, an end of the second insoluble carrier 12 is immersed in the washing solution in the washing solution storage pot 17. Further, the washing solution is sent from the second insoluble carrier 12 to the first insoluble carrier 11, and to the third insoluble carrier 13 by capillary force of the second insoluble carrier 12, the first insoluble carrier 11, and the third insoluble carrier 13.

Further, as described above, the degree of overlapping between the flow path of the sample solution (the first insoluble carrier 11) and the flow path of the washing solution (second insoluble carrier 12 and the third insoluble carrier 13) is minimal. Therefore, while the sample solution is sent, even if unbound analytes and impurities contained in the sample solution accumulate in a downstream area (absorption pad 24) in the direction in which the sample solution is sent, they do not flow to the detection portion again. Hence, it is possible to effectively wash the detection portion without using a large amount of washing solution, and to perform highly accurate detection.

Then, the amplification solution is sent to the detection portion 14 from the amplification solution storage pot 32 provided in the second device part 20. The amplification solution is sent by pressing the amplification solution storage pot 32 toward the first device part 10. When the amplification solution storage pot 32 is pressed, the seal-breaking projection portion provided in the amplification solution storage pot receiving portion 33 breaks the laminated film at the bottom of the amplification solution storage pot 32. Consequently, the amplification solution is sent through the amplification solution injection hole 35, which is provided on the inner surface of the second device part 20, toward the detection portion 14 of the first insoluble carrier 11. At this time, the clearance P is present between the chromatography carrier 23 and the pressing surface 18a. The amplification solution is evenly sent to the chromatography carrier 23, because the clearance P is present. Accordingly, the labeling substance in the complex captured at the detection portion 14 is evenly amplified. Further, the amplification solution is sent vertically to the detection portion 14. When the amplification solution is sent in such a manner, it is possible to reduce the amount of the amplification solution to be used.

After amplification, the detection line 14 is observed and measured, through the observation window 16 of the first device part 10, visually or by using a light source or the like. Therefore, it is possible to detect the analyte at high accuracy and at high sensitivity.

In the above example, a case of using a plurality of kinds of solution (three kinds of solution in this case), i.e., the sample solution, the washing solution (test reagent solution) and the amplification solution, was described. However, the combination of the plurality of kinds of solution is not limited as long as the sample solution is included. The present invention may be applied, for example, to a combination of the sample solution, the amplification solution and the detection solution, or a combination of the sample solution, the test reagent solution and the detection solution, or the like.

Next, various kinds of solution, such as sample solution and test reagent solution, a labeling substance, insoluble carriers and the like that are used in the device for assay of the present invention will be described.

(Sample Solution)

The sample solution that can be analyzed by the device for assay of the present invention is not particularly limited as long as the sample solution may contain an analyte (a bioactive substance, such as a natural product, a toxin and a hormone, an environmental pollutant, or the like). For example, the sample solution may be a biological sample solution. Specifically, a dilution of a biological sample or a dilution of a dried biological sample may be obtained by using a diluent, which will be described later. For example, the biological sample may be body fluid of animals (especially, humans) (for example, blood, blood serum, blood plasma, cerebrospinal fluid, tear fluid, sweat, urine, pus, nasal mucus, and sputum), excrement (for example, feces), an internal organ, tissue, a mucous membrane, skin, a swab sample (swab) that may contain the internal organ, tissue, mucous membrane or skin, a gargle sample, plants, animals and the like.

The sample solution may be used directly without further processing. Alternatively, an extraction solution may be used by obtaining the extraction solution from the sample solution by using an appropriate solvent for extraction. Further, a dilution of the extraction solution may be used by diluting the extraction solution by using an appropriate diluent. Alternatively, a condensed solution of the extraction solution may be used by condensing the extraction solution by using an appropriate method. As the solvent for extraction, a solvent (for example, water, physiological saline, buffer solution or the like), which is normally used in immunoassay, may be used. Alternatively, a water-miscible organic solvent that can directly carry out specifically-binding reaction (for example, antigen-antibody reaction) by being diluted with the aforementioned solvents may be used.

(Labeling Substance)

The labeling substance that may be used in the present invention is not particularly limited as long as the substance is distinguishable by color or detectable by reaction. For example, metal microparticles, colored latex particles, enzymes, and the like that are generally used in immunochromatography may be used. When reduction reaction of metal ions using the labeling substance as a catalyst is utilized to deposit metal on the labeling substance to amplify signals, it is desirable that the labeling substance is metal microparticles because the catalyst activity of the metal microparticles is high.

As the metal microparticles, metal colloid, metal sulfide, other metal alloys, a polymer particle label containing metal or the like may be used. It is desirable that the average particle diameter of the particle (or colloid) is in the range of 1 nm to 10 μm. Examples of the metal microparticles are gold colloid, silver colloid, platinum colloid, iron colloid, aluminum hydroxide colloid, complex colloid thereof, and the like. It is desirable that the metal microparticles are gold colloid, silver colloid, platinum colloid, or complex colloid thereof. Optionally, the gold colloid and the silver colloid may be used, because the gold colloid and the silver colloid having appropriate diameters are red and yellow respectively, and easily identifiable and distinguishable. It is desirable that the average diameter of the metal colloid is in the range of approximately 1 to 500 nm. Optionally, the average diameter may be in the range of 1 to 100 nm.

(Specifically-Binding Substance)

The specifically binding substance is not particularly limited as long as the substance has affinity to the analyte. One of the examples of the specifically binding substance is an antibody. For example, antiserum prepared from the serum of an animal immunized with the analyte, an immunoglobulin fraction purified from antiserum, a monoclonal antibody obtained by cell fusion using splenic cells of an animal immunized with the analyte, and fragments thereof (for example, F(ab')$_2$, Fab, Fab' or Fv) may be used. Such antibodies may be prepared by using ordinary methods.

(Signal Amplification of Labeling Substance)

When assay is performed by using, as a labeling substance, a metal colloid label, a metal sulfide label, a metal alloy label, a polymer particle label containing metal or the like, it is possible to amplify signals of the metal-based label. Specifically, after a complex of the analyte and the labeling substance is formed, the complex is contacted with silver ions and a reducing agent. The silver ions are supplied from a compound containing silver, such as inorganic silver salt and organic silver salt. The silver ions are reduced by the reducing agent, and silver particles are formed. The silver particles are deposited on the metal-based label, as cores. Therefore, signals from the metal-based label are amplified, and highly sensitive analysis of the analyte is possible.

(First Insoluble Carrier)

As illustrated in FIG. 1, the first insoluble carrier (hereinafter, also referred to as a strip for immunochromatography) includes at least one detection line that contains a specifically-binding substance, which can bind to an analyte. The first insoluble carrier is divided into a sample addition pad, a labeling-substance rataining pad, a chromatography carrier, and an absorption pad from the upstream side toward the downstream side of development. The sample addition pad, labeling-substance rataining pad, chromatography carrier, and absorption pad are arranged on an adhesion sheet in this order. It is desirable that a porous material is used as the strip for immunochromatography. For example, a nitrocellulose membrane, a cellulose membrane, an acetyl cellulose membrane, a polysulfone membrane, a polyether sulfone membrane, a nylon membrane, glass fibers, a nonwoven fabric, a cloth, threads or the like may be used (materials for each of the pads and the chromatography carrier will be described later).

In the chromatography carrier, a detection line is formed by immobilizing a specifically-binding substance, which specifically binds to the analyte. Optionally, a control portion may also be formed in the chromatography carrier, if desirable. The specifically-binding substance may be directly immobilized on a part of the chromatography carrier by physical bond (adsorption or the like) or by chemical bond. Alternatively, the specifically-binding substance may be physically or chemically bound to microparticles, such as latex particles, and the microparticles may be trapped and immobilized at a part of the chromatography carrier. Optionally, after the specifically-binding substance is immobilized on the chromatography carrier, the chromatography carrier may be processed to prevent non-specific adsorption, for example, by using inactivated protein or the like.

The labeling-substance rataining pad may be produced by preparing a suspension containing the aforementioned labeling substance, and by coating an appropriate pad (for example, a glass fiber pad) with the suspension, and by drying the pad on which the suspension has been applied. The material of the labeling-substance rataining pad may be, for example, a cellulose filter paper, glass fibers, a nonwoven fabric, or the like.

The sample addition pad is a portion to which the test sample containing the analyte is dropped by spot application or the like. The sample addition pad also has a function for filtering insoluble particles and the like in the sample. The material of the sample addition pad may be a material having uniform properties, such as a cellulose filter paper, glass fibers, polyurethane, polyacetate, cellulose acetate, nylon, and a cotton cloth. However, the material of the sample addition pad is not limited to these materials. Optionally, non-specific adsorption prevention process may be carried out on the sample addition pad in advance. The non-specific adsorption prevention process is performed to prevent the analyte present in the sample from being non-specifically adsorbed onto the material of the sample addition portion (pad) during analysis and to prevent the accuracy of analysis from dropping.

The absorption pad is a portion for physically absorbing the added sample by chromatographic migration. Further, the absorption pad removes an unreacted labeling substance or the like that is not immobilized on the detection portion of the chromatography carrier. The material of the absorption pad may be, for example, water-absorbing materials, such as a cellulose filter paper, a nonwoven fabric, a cloth and cellulose acetate. The speed of chromatography after the leading end of the added sample reaches the absorption portion (pad) differs based on the kind of material, the size or the like of the absorption material. Therefore, a speed appropriate for measurement of the analyte may be set by appropriately selecting the absorption pad.

(Second Insoluble Carrier—Insoluble Carrier for Sending Solution)

The second insoluble carrier is not particularly limited as long as the washing solution or the like can be sent to the first insoluble carrier by capillary force. For example, a glass fiber pad, a cellulose membrane, a nitrocellulose membrane, or the like may be used.

(Third Insoluble Carrier—Insoluble Carrier for Absorption)

The third insoluble carrier is not particularly limited as long as the washing solution or the like that has infiltrated into the first insoluble carrier can be absorbed. For example, cellulose, nitrocellulose, glass fibers, or a mixture thereof may be used.

(Test Reagent Solution)

The term "test reagent solution" refers to a solution containing a reagent (a chemical or the like) that has a supplementary function to the amplification solution or the detection solution. A solution that has a washing function in the assay, i.e., washing solution, is also a test reagent solution. For example, when the amplification solution is a silver ion solution, as described later, a hydroquinone solution, a ferrous ion solution, or the like, which acts as a reducing agent for silver ions, may be used as the test reagent solution. When peroxidase (peroxidase enzyme) is used for amplification, a hydrogen peroxide solution is the test reagent solution. Further, a washing solution that has a washing function in an assay system is also the test reagent solution.

The washing solution is not particularly limited as long as a labeling substance that remains in the chromatography carrier without specifically binding, in other words, a labeling substance that non-specifically remains in the chromatography carrier can be washed. For example, simple water, or a solvent, such as ethanol, may be used alone. Alternatively, a PBS buffer containing 1% BSA, a solution of a surfactant (surface-active agent), or the like may be used. Further, as the washing solution, a solution containing silver ions, as described later, or a solution containing a reducing agent of silver ions may be used. During development, the washing solution washes the labeling substance that non-specifically remains. Therefore, the labeling substance becomes contained in the washing solution on the way of development process. However, the washing solution that does not containing the labeling substance before development is used, because the effect of washing of the washing solution is higher when the labeling substance is not contained. Further, the pH of the washing solution may be adjusted to increase the effect of washing. Alternatively, a washing solution containing a surfactant, protein such as BSA, a high polymer such as polyethylene glycol, or the like may be used.

(Amplification Solution)

The amplification solution produces a colored compound, light emission or the like by catalytic reaction of an agent or chemical or the like in the solution with a labeling substance or an analyte. The amplification solution can amplify signals. The amplification solution is, for example, a silver ion solution, a solution of a phenylenediamine compound and a naphthol compound, or the like. The silver ion solution causes metal silver to precipitate on the metal label by a physical phenomenon. The solution of a phenylenediamine compound and a naphthol compound becomes a dye by action of a peroxidase label and hydrogen peroxide.

Specifically, a so-called developer (developing solution) as described in general publications in the field of photographic chemistry may be used (for example, "Revised Basic Photographic Engineering, Silver Salt Photography", Society of Photographic Science and Technology of Japan, Colona Publishing Co., Ltd., "Photographic Chemistry", A. Sasai, Shashin Kogyo Shuppan, or "Latest Formulation Handbook", S. Kikuchi, et al., Amiko Shuppan). In the present invention, the amplification solution is not particularly limited. Any kind of so-called physical developing solution or developer that contains silver ions, and in which the silver ions in the solution are reduced using metal colloid or the like as development nucleus, may be used as the amplification solution.

Next, a compound containing silver ions for the amplification solution, a reducing agent of silver ions, and the like will be described.

(Compound Containing Silver Ions)

As a compound containing silver ions, an organic silver salt, an inorganic silver salt, or a silver complex may be used. Optionally, silver nitrate, silver acetate, silver lactate, silver thiosulfate, or the like, which is a silver-ion-containing compound that has high solubility in a solvent, such as water, may be used, for example. It is desirable that the silver nitrate is used as the compound. It is desirable that the silver complex is surrounded by ligands including a water-soluble group, such as a hydroxyl group or a sulfone group. For example, hydroxythioether silver or the like may be used.

It is desirable that silver in the inorganic silver salt and the silver complex is generally at 0.001 mol/m$^2$ to 0.2 mol/m$^2$, and optionally, 0.01 mol/m$^2$ to 0.05 mol/m$^2$ per the area of a detection region.

(Reducing Agent of Silver Ions)

As the reducing agent of silver ions, any kinds of inorganic or organic material or a mixture thereof may be used as long as the silver ions can be reduced to silver.

As the inorganic reducing agent, it is desirable to use reducible metal salts or reducible metal complex salts the valences of which can be changed by metal ions, such as $Fe^{2+}$, $V^{2+}$ and $Ti^{3+}$. When the inorganic reducing agent is used, it is necessary to remove or detoxify oxidized ions by forming complexes with the oxidized ions or by reducing the oxidized ions. For example, in a system using $Fe^{+2}$ as the reducing agent, the oxidized ions may be detoxified by forming a complex with $Fe^{3+}$, which is an oxide, using citric acid or EDTA. In the system of the present invention, it is desirable to use the inorganic reducing agent as described above. Optionally, a metal salt containing $Fe^{2+}$ may be used.

Developing base agents that are used for wet-type silver halide photosensitve materials (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes) may be used. Alternatively, other materials that are well known to those skilled in the present field, such as the materials disclosed in U.S. Pat. No. 6,020,117, may be used.

It is desirable to use, as the reducing agent, an ascorbic acid reducing agent. Effective ascorbic acid reducing agents may be an ascorbic acid, an analogue thereof, an isomer thereof, and a derivative thereof. For example, D- or L-ascorbic acid and a sugar derivative thereof (for example, γ-lactoascorbic acid, glucoascorbic acid, fucoascorbic acid, glucoheptoascorbic acid, and maltoascorbic acid), sodium ascorbate, potassium ascorbate, isoascorbic acid (or L-erythroascorbic acid), and a salt thereof (for example, an alkali metal salt, an ammonium salt, or salts known in the present field), and endiol-type ascorbic acid, enaminol-type ascorbic acid, thioenol-type ascorbic acid, or the like may be used. Among these reduing agents, D-, L-, and D,L-ascorbic acid (and an alkali metal salt thereof), and isoascorbic acid (and an alkali metal salt thereof) are desirable. Further, a sodium salt is a desirable salt. Further, a mixture of these reducing agents may be used, if necessary.

(Detection Solution)

The term "detection solution" refers to a solution containing an agent that reacts to a labeling substance, an analyte or the like, and the detection solution changes by such reaction. For example, the color of the detection solution changes by a change in the color of the agent contained in the solution or by production of a colored compound in the solution, or light emission occurs, or the like. For example, the detection solution may be orthocresolphthalein complexone, which exhibits a color by forming a complex with calcium ions, as the analyte. Alternatively, the detection solution may be a copper ion solution, which changes its color by reacting to protein, as the analyte. Further, a solution of a labeled complex that specifically binds to the analyte may be used as the detection solution. For example, labeled DNA and labeled RNA for detecting DNA and RNA by hybridization, antibody sensitized particles and antibody labeled enzymes for detecting antigens, or the like may be used.

(Other Auxiliary Agent)

Besides the test reagent solution, the detection solution and the amplification solution, other auxiliary agents may be used. As the auxiliary agents, the solution may contain a buffer, an antiseptic such as an antioxidant or an organic stabilizer, or a speed regulator. Examples of the buffer are buffers using acetic acid, citric acid, sodium hydroxide, salts thereof, or tris(hydroxymethyl)aminomethane, and other buffers used in general chemical experiments. It is possible to adjust the pH of the amplification solution to an appropriate value by using the buffers.

Next, examples of the device for assay of the present invention will be described in detail.

Example 1

(1) Preparation of Strip for Immunochromatography for Type-A and Type-B Influenza (1-1) Preparation of Anti-Type-A-Influenza and Anti-Type-B-Influenza Antibody-Modified Gold Colloid (1-1-1) Preparation of Anti-Type-A-Influenza Antibody-Modified Gold Colloid 1 ml of 50 mM $KH_2PO_4$ buffer (pH 7.5) was added to 9 ml of a 50 nm diameter gold colloidal solution (EM.GC50, BBI, Ltd.) to adjust the pH of the solution. Further, 1 ml of 90 μg/ml anti-type-A-influenza monoclonal antibody (Anti-Influenza A SPTN-5 7307, Medix Biochemica) solution was added to the gold colloidal solution, and stirred. After stirring, the mixture was kept standing for 10 minutes, and 550 μl of 1% polyethylene glycol (PEG Mw. 20000, Product No. 168-11285, Wako Pure Chemical Industries, Ltd.) aqueous solution was added to the mixture, and stirred. Further, 1.1 ml of 10% bovine serum albumin (BSA Fraction V, Product No. A-7906, SIGMA) aqueous solution was added, and stirred. The solution was centrifuged at 8000×g at 4° C. for 30 minutes (himacCF16RX, Hitachi). The supernatant was removed so that approximately 1 ml of the solution would remain. The gold colloids were dispersed again by using an ultrasonic washing machine. After then, the solution was dispersed in 20 ml of gold colloidal stock solution (20 mM Tris-HCl buffer (pH 8.2), 0.05% PEG (Mw.20000), 150 mM NaCl, 1% BSA, and 0.1% $NaN_3$), and centrifuged again at 8000×g at 4° C. for 30 minutes. The supernatant was removed so that approximately 1 ml of the solution would remain. The gold colloids were dispersed again by using an ultrasonic washing machine, and an antibody-modified gold colloid (50 nm) solution was obtained.

(1-1-2) Preparation of Anti-Type-B-Influenza Antibody-Modified Gold Colloid 1 ml of 50 mM $KH_2PO_4$ buffer (pH 8.0) was added to 9 ml of a 50 nm diameter gold colloidal solution (EM.GC50, BBI, Ltd.) to adjust the pH of the solution. Further, 1 ml of 80 μg/ml anti-type-B-influenza monoclonal antibody (MONOTYPE aby Influenza B Virus (nuclear) Purified 1131, ViroStat, Inc.) solution was added to the gold colloidal solution, and stirred. After stirring, the mixture was kept standing for 10 minutes, and 550 μl of 1% polyethylene glycol (PEG Mw. 20000, Product No. 168-11285, Wako Pure Chemical Industries, Ltd.) aqueous solution was added to the mixture, and stirred. Further, 1.1 ml of 10% bovine serum albumin (BSA Fraction V, Product No. A-7906, SIGMA) aqueous solution was added, and stirred. The solution was centrifuged at 8000×g at 4° C. for 30 minutes (himacCF16RX, Hitachi). The supernatant was removed so that approximately 1 ml of the solution would remain. The gold colloids were dispersed again using an ultrasonic washing machine. After then, the solution was dispersed in 20 ml of gold colloidal stock solution (20 mM Tris-HCl buffer (pH 8.2), 0.05% PEG (Mw.20000), 150 mM NaCl, 1% BSA, and 0.1% $NaN_3$), and centrifuged again at 8000×g at 4° C. for 30 minutes. The supernatant was removed so that approximately 1 ml of the solution would remain. The gold colloids were dispersed again by using an ultrasonic washing machine, and an antibody-modified gold colloid (50 nm) solution was obtained.

(1-2) Preparation of Gold Colloidal Antibody Retaining Pad (Labeling Substance Retaining Pad)

The anti-type-A-Influenza antibody-modified gold colloid solution and the anti-type-B-Influenza antibody-modified gold colloid solution that were prepared in the above process, (1-1), were mixed at 1:1, and diluted with a coating solution for gold colloid (20 mM Tris-Hcl buffer (pH 8.2), 0.05% PEG (Mw: 20000), and 5% sucrose) and water so that the OD (optical density) of the diluted solution at 520 nm would become 3.0. This solution was evenly applied to glass fiber pads (Glass Fiber Conjugate Pad, Millipore) cut to a size of 8 mm×150 mm, and 0.8 ml of solution was applied to each of the pads. The pads were dried under reduced pressure overnight to obtain gold colloidal antibody retaining pads.

(1-3) Preparation of Antibody-Immobilized Membrane (Chromatography Carrier)

An antibody-immobilized membrane was prepared by immobilizing an antibody on a nitrocellulose membrane (Hi-Flow Plus HF120 with plastic lining, Millipore) cut to a size of 25 mm×200 mm, as follows. The longer side of the membrane was placed on the down side, and a solution of anti-type-A-influenza monoclonal antibody for immobilization (Anti-Influenza A SPTN-5 7307, Medix Biochemica) prepared at 1.5 mg/ml was applied to a position of the membrane at 7 mm from the bottom thereof. The solution was applied in line form with a width of approximately 0.7 mm by using an inkjet type coater (BioDot Ltd.). Similarly, a solution of anti-type-B-influenza monoclonal antibody for immobilization (MONOTYPE aby Influenza B Virus (nuclear) Purified 1131, ViroStat, Inc.) prepared at 1.5 mg/ml was applied to a position of the membrane at 10 mm from the bottom thereof. The solution was applied in line form with a width of approximately 0.7 mm. Similarly, an anti-mouse IgG antibody for control (anti-mouse IgG (H+L), rabbit F(ab')$_2$, Product No. 566-70621, Wako Pure Chemical Industries, Ltd.) solution prepared at 0.5 mg/ml was applied, in line form, to a position of the membrane at 13 mm from the bottom thereof. The coated membrane was dried at 50° C. for 30 minutes by a hot-air dryer. The membrane was immersed in 500 ml of 50 mM borate buffer (pH 8.5) containing a blocking solution (0.5 wt % casein (milk-derived product, Product No. 030-01505, Wako Pure Chemical Industries, Ltd.)) in a vat, and kept standing for 30 minutes. After then, the membrane was moved to another vat that is similar to the aforementioned vat, and immersed in 500 ml of washing-stabilizing solution (50 mM Tris-HCl (pH 7.5) buffer containing 0.5 wt % sucrose and 0.05 wt % sodium cholate) in the vat, and kept standing for 30 minutes. The membrane was removed from the solution, and dried overnight at room temperature to give an antibody-immobilized membrane (line coating or application).

(1-4) Preparation of Strip for Immunochromatography

The antibody-immobilized membrane prepared in the above process, (1-3), was attached to a back adhesive sheet (20 mm×150 mm, ARcare9020, NIPPN TechnoCluster, Inc.) in such a manner that they overlap with each other by 3 mm. At this time, the back adhesive sheet was attached to the longer side of the membrane on the anti-type-A-influenza antibody side. Next, the gold colloidal antibody retaining pad prepared in the above process, (1-2), was attached to the antibody-immobilized membrane in such a manner that they overlap with each other by 3 mm. A sample addition pad (glass fiber pad cut to 18 mm×150 mm (Glass Fiber Conjugate Pad, Millipore)) was set to the longer side of the back adhesion sheet, the longer side to which the membrane was not attached, and attached in such a manner that the gold colloidal antibody retaining pad is held or covered by the sample addition pad. Further, the back adhesion sheet (20 mm×150 mm) and the absorption pad (20 mm×150 mm) were attached to the anti-mouse IgG antibody for control line side of the membrane in such a manner that the portion of the membrane is held between the back adhesion sheet and the absorption pad. A member (immunochromatography main member), which was obtained by placing these elements one on another as described above, was cut by using a guillotine cutter (CM4000, NIPPN TechnoCluster, Inc.). The member was cut parallel to the short side thereof so that the width of the obtained strip is 7 mm. Accordingly, a strip for immunochromatography having a size of 7 mm×60 mm was produced.

(1-5) Preparation of Silver Amplification Solution (1-5-1-1) Preparation of Reducing Agent Solution A 23.6 ml of 1 mol/l iron nitrate aqueous solution was prepared by dissolving iron nitrate (III) nonahydrate (Wako Pure Chemical Industries, Ltd., 095-00995) in 290 g of water. Further, 13.1 g of citric acid (Wako Pure Chemical Industries, Ltd., 038-06925) was dissolved in the solution. After all of them were dissolved, 36 ml of nitric acid (10 wt %) was added with stirring by using a stirrer. Further, 60.8 g of ammonium iron (II) sulfate hexahydrate (Wako Pure Chemical Industries, Ltd., 091-00855) was added to the solution, and reducing agent solution A was obtained.

(1-5-1-2) Preparation of Reducing Agent Solution B 23.6 ml of 1 mol/l iron nitrate aqueous solution was prepared by dissolving iron nitrate (III) nonahydrate (Wako Pure Chemical Industries, Ltd., 095-00995) in 290 g of water. Further, 13.1 g of citric acid (Wako Pure Chemical Industries, Ltd., 038-06925), 0.2 g of dodecylamine (Wako Pure Chemical Industries, Ltd., 123-00246), and 0.2 g of 1,12-dodecanediamine (Wako Pure Chemical Industries, Ltd., 042-25702) were dissolved in the solution. After all of them were dissolved, 36 ml of nitric acid (10 wt p) was added with stirring by using a stirrer. Further, 40.5 g of ammonium iron (II) sulfate hexahydrate (Wako Pure Chemical Industries, Ltd., 091-00855) was added to the solution, and reducing agent solution B was obtained.

(1-5-1-3) Preparation of Reducing Agent Solution C 36 ml of nitric acid (10 w %), 0.2 g of dodecylamine (Wako Pure Chemical Industries, Ltd., 123-00246), and 0.2 g of 1,12-dodecanediamine (Wako Pure Chemical Industries, Ltd., 042-25702) were dissolved in 320 g of water. After all of them were dissolved, 30.4 g of ammonium iron (II) sulfate hexahydrate (Wako Pure Chemical Industries, Ltd., 091-00855) was added with stirring by using a stirrer, and reducing agent solution C was obtained.

(1-5-2-1) Preparation of Silver Ion Solution A 8 ml of silver nitrate solution (containing 10 g of silver nitrate) and 24 ml of 1 mol/l iron nitrate aqueous solution were added to 66 g of water. Further, this solution was mixed with a solution that had been prepared, in advance, by dissolving 5.9 ml of nitric acid (10 wt %), 0.1 g of dodecylamine (Wako Pure Chemical Industries, Ltd., 123-00246), and 0.1 g of surfactant $C_{12}H_{25}$—$C_6H_4$—O—$(CH_2CH_2O)_{50}$H in 47.6 g of water, and silver ion solution A was obtained.

(1-5-2-2) Preparation of Silver Ion Solution B 8 ml of silver nitrate solution (containing 10 g of silver nitrate) was added to 90 g of water. Further, this solution was mixed with a solution that had been prepared, in advance, by dissolving 5.9 ml of nitric acid (10 wt %) and 0.1 g of surfactant $C_{12}H_{25}$—$C_6H_4$—O—$(CH_2CH_2O)_{50}$H in 47.6 g of water, and silver ion solution B was obtained.

(1-5-2-3) Preparation of Silver Ion Solution C 16 ml of silver nitrate solution (containing 10 g of silver nitrate) was added to 82 g of water. Further, this solution was mixed with a solution that had been prepared, in advance, by dissolving 5.9 ml of nitric acid (10 wt %) and 0.1 g of acetyleneglycol-based surfactant, Surfinol 465 (Nisshin Chemical Industry Co., Ltd.) in 47.6 g of water, and silver ion solution C was obtained.

Example 1

Production of Device for Assay

As illustrated in FIG. 1, the strip for immunochromatography was loaded into the first device part 10 (that is made of polypropylene and made by injection molding) illustrated in FIG. 2. Further, glass fiber pads (Glass Fiber Conjugate Pad, Millipore), as the second insoluble carrier 12 and the third insoluble carrier 13, were loaded into the first device part 10. Meanwhile, 150 μl of reducing agent solution that had been prepared in the above process (1-5-1) was poured into the washing solution storage pot 17, and the washing solution storage pot 17 was sealed by thermal lamination using an aluminum laminated sheet (NewADM, Sunrise Co.). Further, the second device part 20 was fitted with the first device part 10. Meanwhile, 110 μl of silver ion solution that had been prepared in the above process (1-5-2) was poured into the amplification solution storage pot 32, and the amplification solution storage pot 32 was sealed by an aluminum laminated sheet. The amplification solution storage pot 32 was mounted in the pot receiving portion 33, as illustrated in FIG. 1.

(Spot Application and Development of Antigen Solution)

As sample solutions, Quick S-Influ A•B "Seiken" negative/positive controls (Product No. 322968, DENKA SEIKEN Co., Ltd.) were used. The positive control solution was diluted with a PBS buffer containing 1 mass % BSA. The detection limits of Quick S-Influ A•B "Seiken" by using immunochromatography detection kit that is available in the market, "Capillia Flu A•B" (Alfresa Pharma Corporation), were 1/40 for both of type A and type B. Here, a PBS buffer containing 1 mass % BSA was used, and A-type positive control serial dilutions of 1/80, 1/160, 1/320, 1/640, 1/1280, 1/2560 and 1/5120 were prepared as sample solutions. Further, 140 μl of prepared sample solution was dropped through the sample solution injection hole, and kept standing for 10 minutes.

(Pressing Second and Third Insoluble Carriers)

After the sample solution was developed for 10 minutes, the pressing portion 34 of the second device part 20 was pressed at the force of 10 N to bend the second device part 20, thereby pressing the insoluble carrier for sending solution (second insoluble carrier 12) onto the membrane. At this time, the magnitude of pressing (the distance of displacement by pressing) is restricted by contact between the rib 15 of the first device part 10 and the second device part 20. The height of the rib 15 was adjusted so that the portion of the insoluble carrier for sending solution that is placed, by the second device part 20, in contact with the surface of the membrane of the strip for immunochromatography (first insoluble carrier 11) would be pressed down to the thickness of 0.2 mm. Further, the form of the pressing unit of the second device part 20 was adjusted so that the clearance between the membrane surface of the strip for immunochromatography (first insoluble carrier 11) and the pressing surface 18a of the second device part would become 0.005 mm.

(Washing)

When 30 seconds passed after the insoluble carrier for sending solution had been pressed, the seal-breaking unit 19 of the second device part 20 was pressed. The seal-breaking unit 19, together with the insoluble carrier for sending solution, broke the aluminum sheet, and the insoluble carrier 12 was immersed in the reducing agent solution. Accordingly, the reducing agent solution was developed in the strip for immunochromatography, and the solution was continued to be sent for three minutes. Through this step, the strip for immunochromatography was immersed in the reducing agent solution A. Further, material which had not been specifically adsorbed was washed away.

(Amplification of Signals by Amplification Solution)

The solution storage pot 32 mounted in the second device part 20 was pressed down to break the sealing thereof by the projection portion. Accordingly, the silver ion solution A was discharged from the solution storage pot 32, and poured through the injection hole. The silver ion solution A was loaded into the clearance between the membrane surface and the pressing unit of the second device part, and amplified the gold collide label adsorbed at the detection line for one minute.

With respect to the combination of reducing agent solution B and silver ion solution B, (Washing) and (Amplification of Signals by Amplification Solution) were performed in a matter similar to the above process. Further, with respect to the combination of reducing agent solution C and silver ion solution C, (Washing) and (Amplification of Signals by Amplification Solution) were performed in a matter similar to the above process.

Example 2

Amplification was performed in a manner similar to Example 1 except that the form of the pressing unit of the second device part was adjusted so that the clearance between the membrane surface of the strip for immunochromatography (first insoluble carrier 11) and the pressing unit of the second device part would become 0.2 mm.

Example 3

Amplification was performed in a manner similar to Example 1 except that the form of the pressing unit of the second device part was adjusted so that the clearance between the membrane surface of the strip for immunochromatography (first insoluble carrier 11) and the pressing unit of the second device part would become 1 mm.

Example 4

Amplification was performed in a manner similar to Example 1 except that the form of the pressing unit of the second device part was adjusted so that the clearance between the membrane surface of the strip for immunochromatography (first insoluble carrier 11) and the pressing unit of the second device part would become 1.2

Comparative Example 1

Amplification was performed in a manner similar to Example 1 except that the pressing unit of the second device part was removed, and that a clearance from the membrane surface was not formed, and that 110 µl of silver ion solution was supplied by dropping it onto the membrane surface.

Comparative Example 2

Amplification was performed in a manner similar to Example 1 except that the silver ion solution was not supplied from the solution storage pot, and that 110 µl of silver ion solution was supplied by directly dropping it onto the sample pad.

Comparative Example 3

Amplification was performed in a manner similar to Example 1 except that the silver ion solution was not supplied from the solution storage pot, and that 110 µl of amplification that had been prepared by mixing the silver ion solution and the reducing agent solution at 1:4 was supplied by directly dropping it onto the sample pad.

<Evaluation>

After amplification, the device was visually observed from the observation window 16 of the first device part 10. The lowest concentration of the serial dilutions of the sample in which the positive reaction was confirmed was judged as the detection sensitivity limit. The result is shown in Table 1.

TABLE 1

| | METHOD FOR SUPPLYING AMPLIFICATION SOLUTION | AMPLIFICATION SURFACE CONDITION | DETECTION SENSITIVITY REDUCING AGENT · SILVER ION SOLUTION A | REDUCING AGENT · SILVER ION SOLUTION B | REDUCING AGENT · SILVER ION SOLUTION C | STATE LOADING AMPLIFICATION SOLUTION |
|---|---|---|---|---|---|---|
| EXAMPLE 1 | LOADING INTO CLEARANCE OF 0.005 mm | ○ | 1/2560 | 1/2560 | 1/2560 | VERY RARE, BUT SOLUTION DOES NOT SPREAD TO SOME PORTION |
| EXAMPLE 2 | LOADING INTO CLEARANCE OF 0.2 mm | ○ | 1/2560 | 1/5120 | 1/5120 | EXCELLENT SURFACE CONDITION |
| EXAMPLE 3 | LOADING INTO CLEARANCE OF 1 mm | ○ | 1/2560 | 1/5120 | 1/5120 | EXCELLENT SURFACE CONDITION |
| EXAMPLE 4 | LOADING INTO CLEARANCE OF 1.2 mm | ○ | 1/2560 | 1/2560 | 1/5120 | VERY RARE, BUT SOLUTION DOES NOT SPREAD TO SOME PORTION |
| COMPARATIVE EXAMPLE 1 | NO CLEARANCE, DROP AMPLIFICATION SOLUTION ONTO INSOLUBLE CARRIER | x | (1/2560) | (1/2560) | (1/2560) | SOLUTION DOES NOT SPREAD EVENLY, AND UNAMPLIFIED PORTION REMAINS |
| COMPARATIVE EXAMPLE 2 | DROP AMPLIFICATION SOLUTION ONTO SAMPLE PAD | x | UNDETECTABLE | UNDETECTABLE | UNDETECTABLE | NOT AMPLIFIED |
| COMPARATIVE EXAMPLE 3 | DROP MIXTURE OF TEST REAGENT SOLUTION AND AMPLIFICATION SOLUTION ONTO SAMPLE PAD | x | 1/160 | 1/160 | 1/160 | AMPLIFIED, BUT VERY UNEVEN |

As Table 1 clearly shows, the detection sensitivities of Examples 1 through 4 were in the range of 1/2560 to 1/5120, which indicate extremely high sensitivity. Further, the amplification solution was evenly loaded into the clearance portion P. In Example 1, the gap (distance) of the clearance portion was 0.005 mm, which is narrow. Therefore, it was very rare, but the amplification solution did not spread to some portion in some cases. In Example 4, the gap (distance) of the clearance portion was 1.2 mm, which is wide. Hence, capillary force did not act sufficiently. Therefore, it was rare, but the amplification solution did not spread to some portion in some cases. This result shows that it is desirable that the clearance portion P is adjusted to the range of 0.01 to 1 mm.

In contrast, in Comparative Example 1, no clearance portion P was provided, and the amplification solution was dropped from the upper side of the first device part 10. In Comparative Example 1, the detection sensitivity was substantially the same as the detection sensitivities of the examples. However, in Comparative Example 1, the amplification solution did not spread evenly, and an unamplified portion remained at the detection line. In Comparative Example 2, in which the amplification solution was directly dropped onto the sample pad, no amplification was performed, because the amplification solution flowed in the membrane, which is the first insoluble carrier, and the reducing agent solution present in the membrane was pushed away to the absorption pad. Therefore, the reduction reaction did not progress, and it was impossible to perform amplification. Further, when a mixture of the test reagent solution and the amplification solution was dropped onto the sample pad, amplification was performed, but it was extremely uneven. The reason why the amplification was uneven was that components contained in the reducing agent and the amplification solution were not distributed evenly on the membrane because of a difference in the molecular mutual reaction with the membrane, and the reaction did not progress evenly.

As described above, in the device for assay of the present invention, the pressing unit having a pressing surface is provided on the inner surface of the second device part that faces the detection portion of the first insoluble carrier. Further, the pressing surface, which is parallel to the detection portion of the first insoluble carrier, is displaced by being pressed toward the detection portion, and presses, from the upper side of the first insoluble carrier, the second insoluble carrier and the third insoluble carrier onto the first insoluble carrier. Therefore, when the pressing portion is pressed from the outer surface of the second device part toward the first device part, the pressing surface of the pressing unit is displaced, and a clearance is formed between the pressing surface of the pressing portion and the detection portion. Therefore, it is possible to evenly develop solution by capillary force of the clearance. Hence, highly accurate and highly sensitive measurement is possible.

The invention claimed is:

1. A device for assay, the device comprising:
a complex part including a first device part and a second device part, wherein the first device part includes a first insoluble carrier housed therein, the first insoluble carrier having a detection portion containing a substance that specifically binds to an analyte, and wherein the second device part has a hole for injecting solution into the first device part, and wherein a second insoluble carrier for developing the solution and a third insoluble carrier for absorbing the solution are housed in the complex part, and wherein the second insoluble carrier and the third insoluble carrier are kept in such a manner that the second insoluble carrier and the third insoluble carrier are partially superimposed and fixed at the detection portion of the first insoluble carrier, and wherein the first insoluble carrier, the second insoluble carrier and the third insoluble carrier are housed in such a manner that they are not in contact with each other, and wherein a pressing unit having a pressing surface that faces the detection portion of the first insoluble carrier is provided in the second device part that faces the detection portion of the first insoluble carrier, and wherein the pressing surface is displaced by being pressed toward the detection portion, and presses, from the upper side of the first insoluble carrier, the second insoluble carrier and the third insoluble carrier onto the first insoluble carrier,
wherein when the pressing unit has been pressed toward the detection portion, a clearance between the detection portion and the pressing surface is in the range of 0.01 to 1 mm;
wherein a rib that regulates the displacement of the pressing surface by abutting a part of the pressing unit is provided on an inner surface of the first device part, the inner surface facing the pressing unit;
wherein a liquid storing pot capable of sending liquids to the gap between the detection portion and the pressing surface is provided in each of the first device part and the second device part, the liquid storing pots being sealed with laminated films; and
wherein a reagent solution is injected into the liquid storing pot provided in the first device part, and an amplifying solution that contains silver ions is injected into the second liquid storing pot.

* * * * *